United States Patent
Im

(10) Patent No.: US 11,291,521 B2
(45) Date of Patent: Apr. 5, 2022

(54) SURGERY ASSISTING DEVICE USING AUGMENTED REALITY

(71) Applicant: Seung Joon Im, Seoul (KR)

(72) Inventor: Seung Joon Im, Seoul (KR)

( * ) Notice: Subject to any disclaimer, the term of this patent is extended or adjusted under 35 U.S.C. 154(b) by 0 days.

(21) Appl. No.: 17/293,335

(22) PCT Filed: Nov. 8, 2019

(86) PCT No.: PCT/KR2019/015171
§ 371 (c)(1),
(2) Date: May 12, 2021

(87) PCT Pub. No.: WO2020/101283
PCT Pub. Date: May 22, 2020

(65) Prior Publication Data
US 2021/0401533 A1  Dec. 30, 2021

(30) Foreign Application Priority Data
Nov. 14, 2018 (KR) .................. 10-2018-0139902

(51) Int. Cl.
| | |
|---|---|
| A61B 90/00 | (2016.01) |
| A61B 34/20 | (2016.01) |
| G06F 3/01 | (2006.01) |
| A61B 90/50 | (2016.01) |
| A61B 34/00 | (2016.01) |
| G06F 3/12 | (2006.01) |
| G16H 30/20 | (2018.01) |

(52) U.S. Cl.
CPC ............ *A61B 90/361* (2016.02); *A61B 34/20* (2016.02); *A61B 34/25* (2016.02); *A61B 90/37* (2016.02); *A61B 90/50* (2016.02); *G06F 3/011* (2013.01); *G06F 3/12* (2013.01); *G16H 30/20* (2018.01); *A61B 2034/2048* (2016.02); *A61B 2034/2065* (2016.02); *A61B 2034/252* (2016.02); *A61B 2034/256* (2016.02); *A61B 2090/365* (2016.02); *A61B 2090/502* (2016.02)

(58) Field of Classification Search
None
See application file for complete search history.

(56) References Cited

U.S. PATENT DOCUMENTS

| | | | |
|---|---|---|---|
| 9,645,785 B1 | 5/2017 | Hannaford et al. | |
| 2014/0073907 A1* | 3/2014 | Kumar | A61B 10/0241 600/414 |
| 2016/0154620 A1 | 6/2016 | Tsuda et al. | |
| 2018/0032130 A1 | 2/2018 | Meglan | |
| 2018/0184974 A1 | 7/2018 | Cimenser et al. | |

FOREIGN PATENT DOCUMENTS

| | | |
|---|---|---|
| KR | 10-2015-0024199 A | 3/2015 |
| KR | 10-2016-0033721 A | 3/2016 |
| KR | 10-2017-0093422 A | 8/2017 |

\* cited by examiner

*Primary Examiner* — David H Chu
(74) *Attorney, Agent, or Firm* — Birch, Stewart, Kolasch & Birch, LLP

(57) ABSTRACT

A surgery assisting device using augmented reality includes: a camera configured to record an affected area or a surgical site of a patient; wireless transmission equipment configured to receive and transmit an image recorded by the camera in real time; smart glasses configured to display the image transmitted by the wireless transmission equipment to a wearer; and an Augmented Reality (AR) server configured to add augmented reality to the image and provide the wearer with the augmented reality.

16 Claims, 7 Drawing Sheets

[FIG. 1]
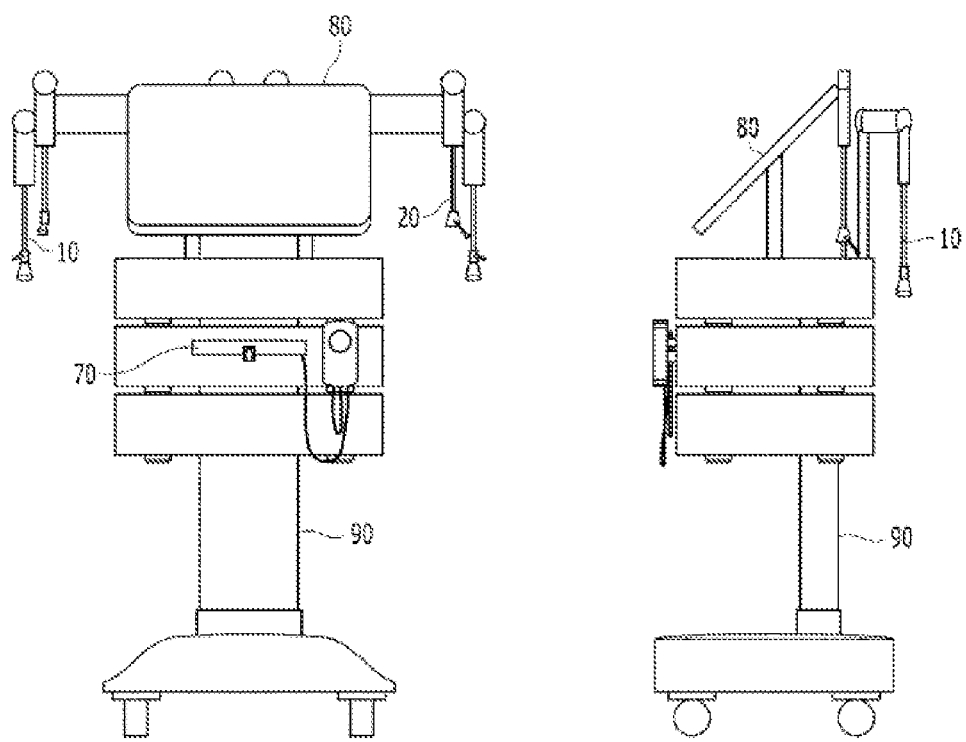
[FIG. 2]
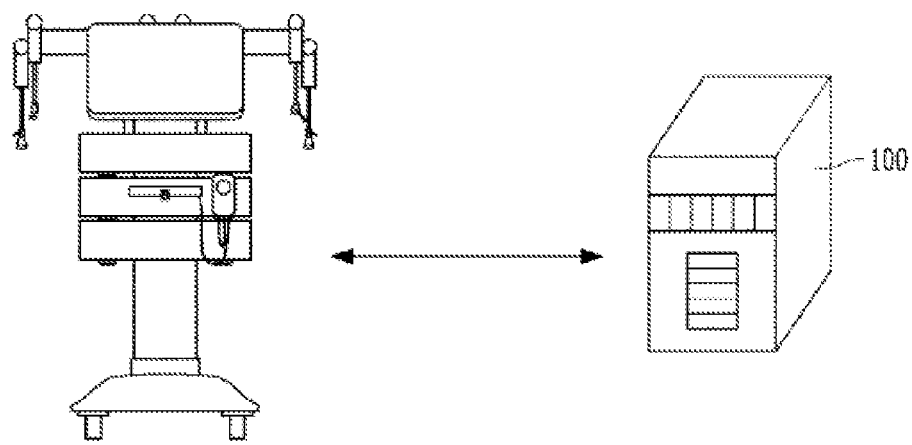

[FIG. 3]
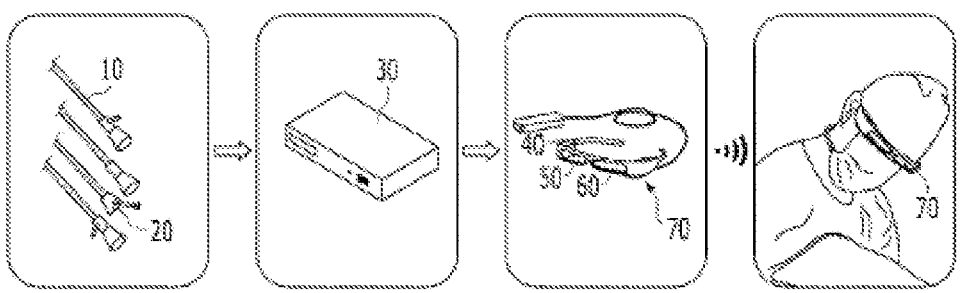
[FIG. 4]
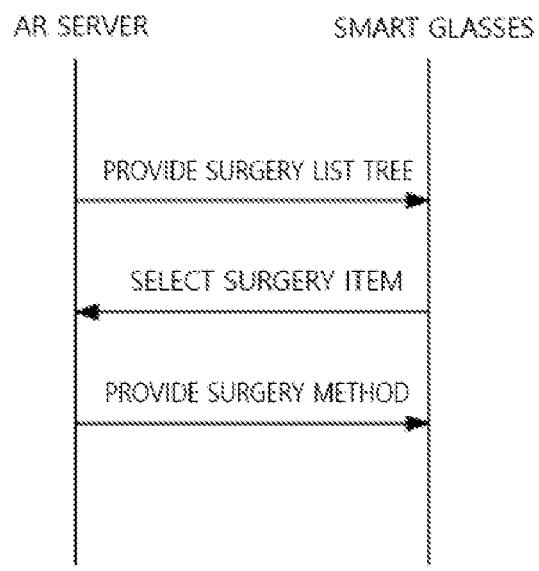

[FIG. 5]
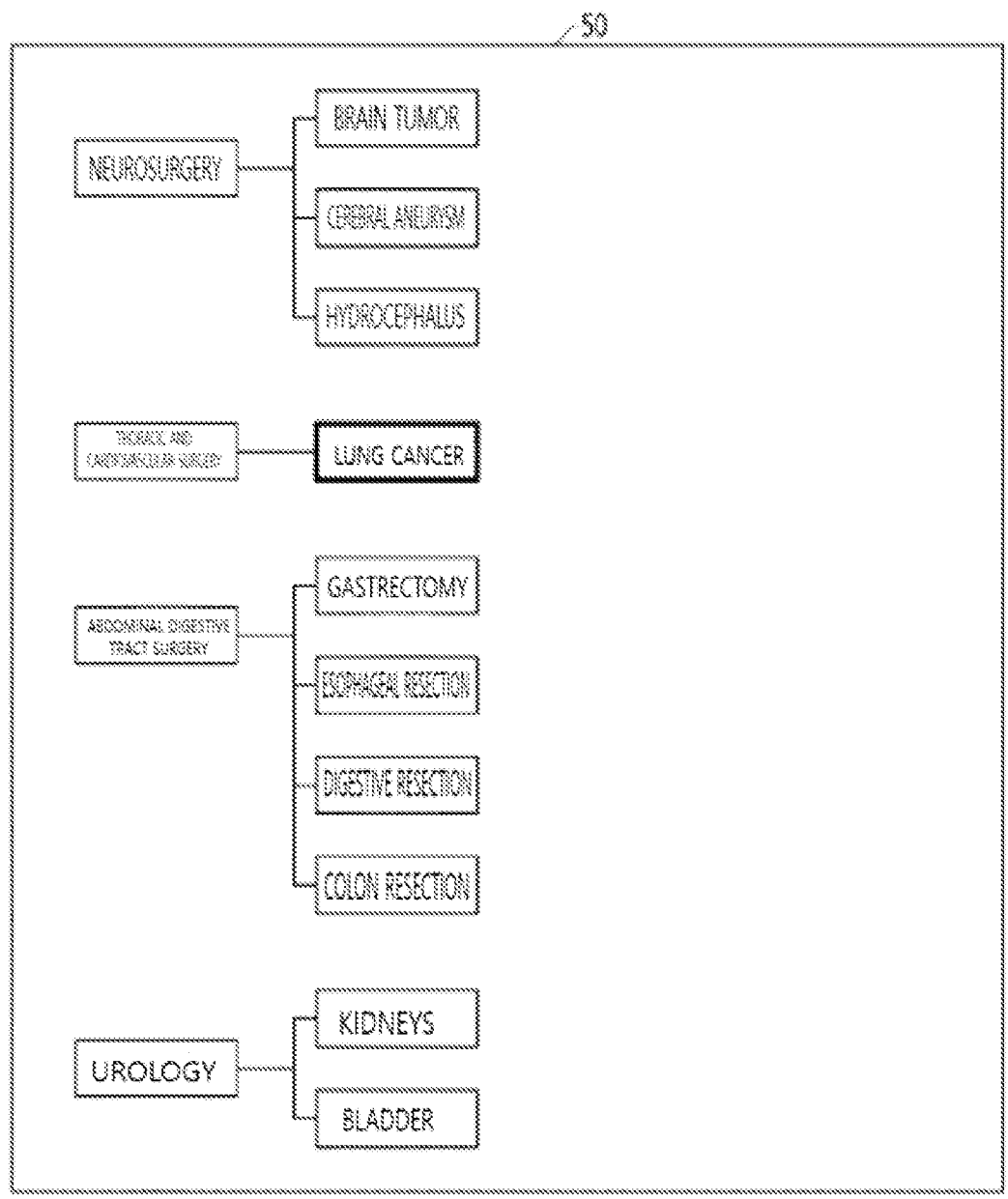

[FIG. 6]
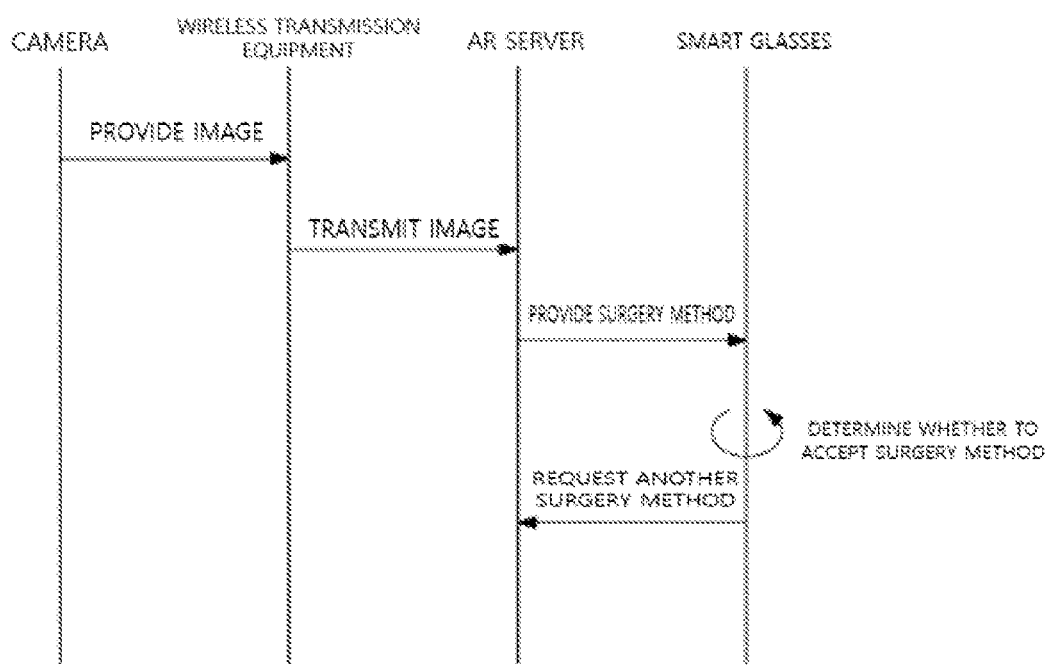
[FIG. 7]
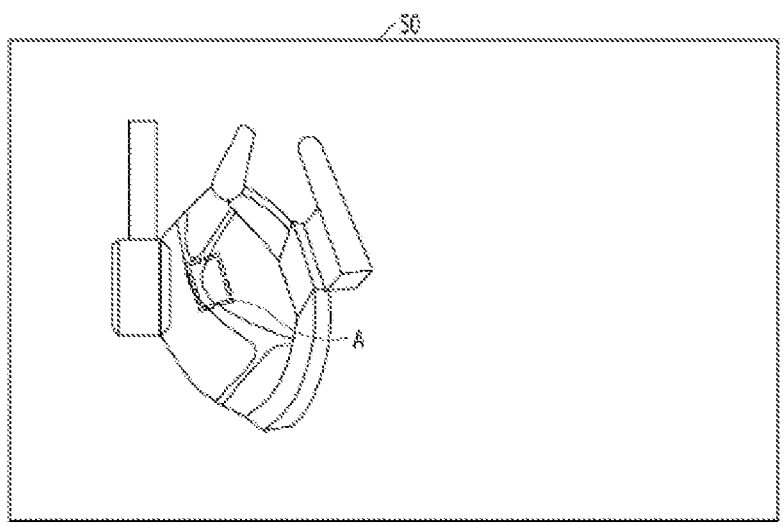

[FIG. 8]
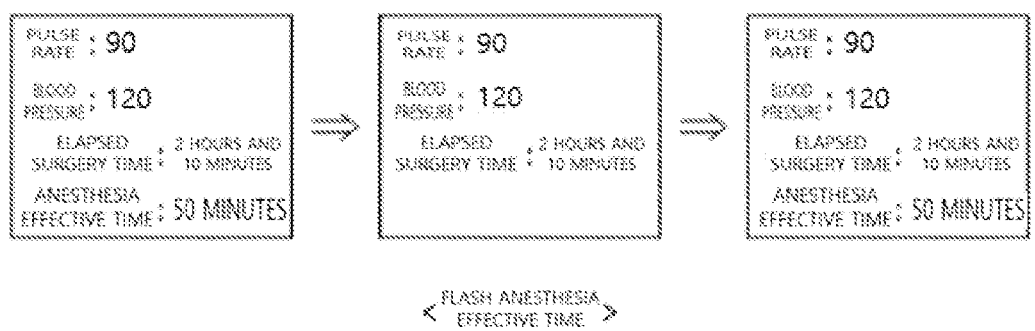
[FIG. 9]
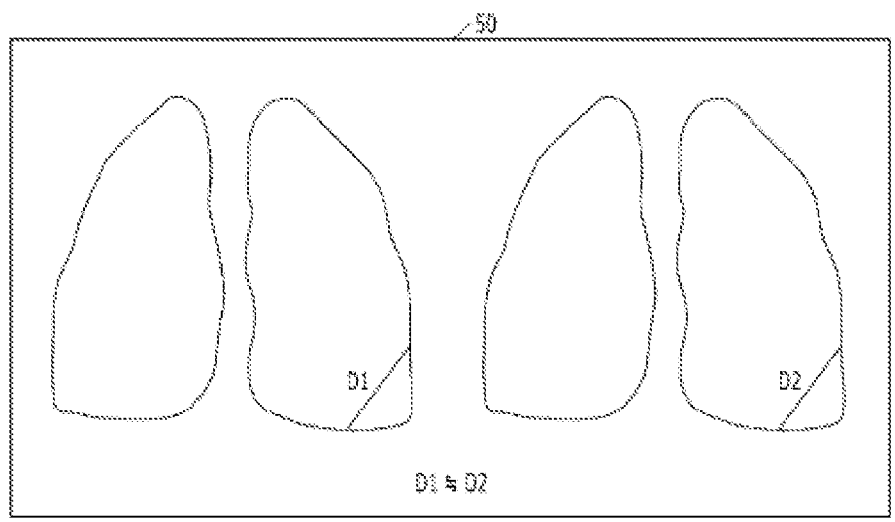

[FIG. 10]
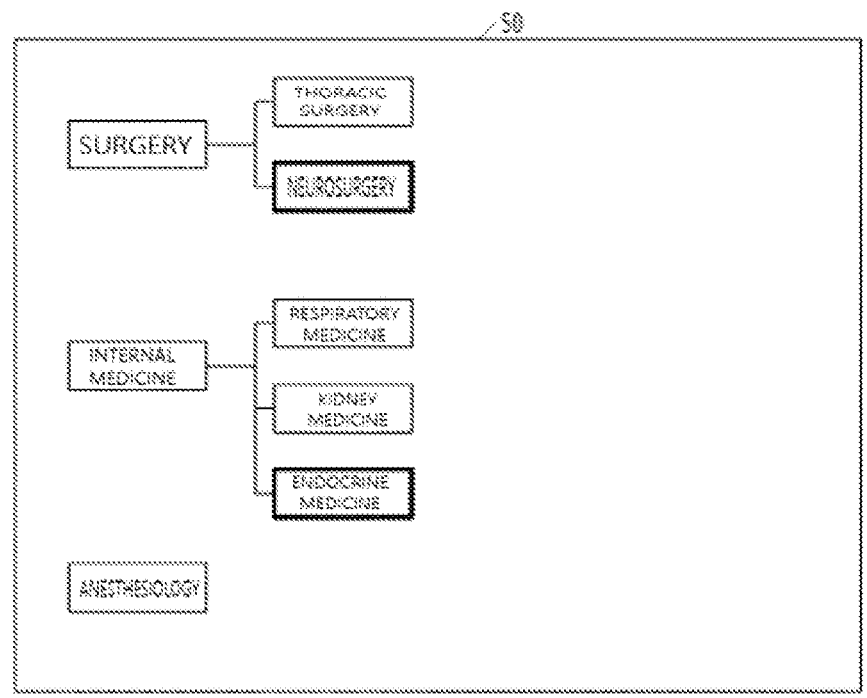

[FIG. 11]
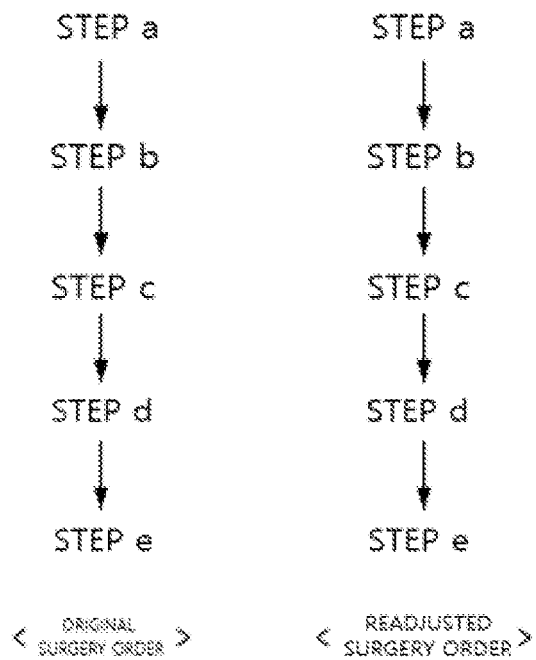
[FIG. 12]
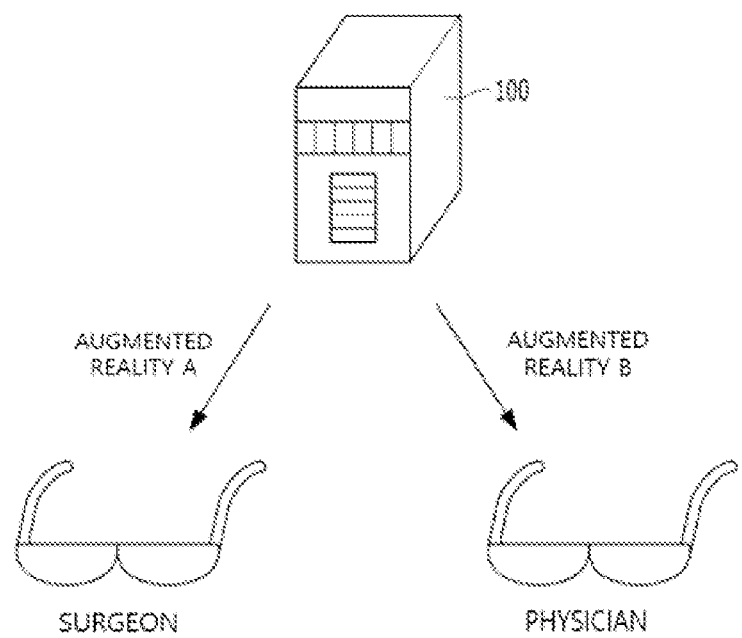

SURGERY ASSISTING DEVICE USING AUGMENTED REALITY

CROSS REFERENCE TO RELATED APPLICATIONS

This application is the National Phase of PCT/KR2019/015171 filed on Nov. 8, 2019, which claims priority under 35 U.S.C. § 119(a) to Korean Patent Application No. 10-2018-0139902 filed in the Republic of Korea on Nov. 14, 2018, all of these applications are hereby expressly incorporated by reference into the present application.

TECHNICAL FIELD

The present invention relates to a surgery assisting device using augmented reality, and more particularly, to a surgery assisting device using augmented reality which provides smart glasses worn by a wearer with various information related to a surgery by using augmented reality to enable a successful surgery.

BACKGROUND ART

In the related art, when a surgery, such as cutting a specific part inside the body, is performed, laparotomy was performed, but recently, a part of the body is perforated, a camera is inserted through the perforation, and the image recorded by the camera is displayed on a monitor, and a surgeon performs surgery while looking at the monitor.

In addition, even when areas, such as the inside of the mouth, that are difficult to see with the naked eyes, are treated, the image recorded through the camera is displayed on a monitor and then the treatment is performed by using the image. Otherwise, a surgery or medical procedure is easily performed by enlarging a specific body part by using a loupe.

However, the surgery and treatment method in the related art (see Korean Patent Application No. 10-2018-7007193) simply enlarges and displays the patient's affected area or surgical site on a monitor, and does not display information helpful for surgery on the monitor, so that there is a problem in that the surgery and treatment method in the related art is nothing more than a fragmentary auxiliary device.

DISCLOSURE

Technical Problem

In order to solve the problem, there is a need for a surgery assisting device using augmented reality, which is practically helpful in surgery by displaying information helpful for surgery on an image of a surgical site recorded by a camera.

An object to be solved by the present invention is to provide a surgery assisting device using augmented reality, which provides a wearer with information practically helpful for surgery by applying augmented reality to an image of a surgical site recorded by a camera and displaying the image on smart glasses of the wearer.

The objects of the present invention are not limited to the foregoing objects, and those skilled in the art will clearly understand other non-mentioned objects through the description below.

Technical Solution

In order to solve the object, a surgery assisting device using augmented reality according to an exemplary embodiment of the present invention includes: a camera configured to record an affected area or a surgical site of a patient; wireless transmission equipment configured to receive and transmit an image recorded by the camera in real time; smart glasses configured to display the image transmitted by the wireless transmission equipment to a wearer; and an Augmented Reality (AR) server configured to add augmented reality to the image and provide the wearer with the augmented reality.

In order to solve the object, a surgery assisting device using augmented reality according to another exemplary embodiment of the present invention includes: a camera configured to record an affected area or a surgical site of a patient; wireless transmission equipment configured to receive and transmit an image recorded by the camera in real time; smart glasses configured to display the image transmitted by the wireless transmission equipment to a wearer; an Augmented Reality (AR) server configured to add augmented reality to the image and provide the wearer with an AR image to which the augmented reality is applied; and a data storage unit configured to store any one or both the recorded image recorded by the camera and the AR image, in which the AR server categorizes any one or both the recorded image recorded by the camera and the AR image based on a predetermined category item, and classifies image segmentations, which are generated as a result of the performance of the categorization and to which category information is added, based on each category and stores the classified image segmentations in the data storage unit, and when a collaborative medical treatment request is generated, the AR server selects a collaborative medical specialist according to a predetermined collaborative medical specialist selection reference, and selects an image segmentation required for the selected collaborative medical specialist among the image segmentations classified based on each category stored in the data storage unit and provides the selected collaborative medical specialist with the selected image segmentation.

Advantageous Effects

According to the present invention, it is possible to provide a wearer with information practically helpful for surgery by applying augmented reality to an image of a surgical site recorded by a camera and displaying the image on smart glasses of the wearer.

DESCRIPTION OF DRAWINGS

FIGS. 1 and 2 are diagrams illustrating partial configurations of a surgery assisting device using augmented reality according to an exemplary embodiment of the present invention.

FIG. 3 is a conceptual diagram of the surgery assisting device using augmented reality according to the exemplary embodiment of the present invention.

FIGS. 4 and 5 are diagrams illustrating an exemplary embodiment in which the surgery assisting device using augmented reality according to the exemplary embodiment of the present invention provides a surgery list tree.

FIG. 6 is a diagram illustrating an exemplary embodiment in which the surgery assisting device using augmented reality according to the exemplary embodiment of the present invention presents a surgery method based on a provided image.

FIG. 7 is a diagram illustrating a case where the surgery assisting device using augmented reality according to the exemplary embodiment of the present invention emphasizes a surgical site.

FIG. 8 is a diagram illustrating a case where the surgery assisting device using augmented reality according to the exemplary embodiment of the present invention flashes information departing from a safety range among surgical information.

FIG. 9 is a diagram illustrating a case where the surgery assisting device using augmented reality according to the exemplary embodiment of the present invention presents an actual surgery progress state and an ideal surgery progress state to a wearer.

FIG. 10 is a diagram illustrating an exemplary embodiment in which the surgery assisting device using augmented reality according to the exemplary embodiment of the present invention provides a collaboration list tree.

FIG. 11 is a diagram illustrating the case where the surgery assisting device using augmented reality according to the exemplary embodiment of the present invention readjusts the order of a surgery method and provides the surgery method again.

FIG. 12 is a diagram illustrating a state where a surgery assisting device using augmented reality according to another exemplary embodiment of the present invention provides a plurality of smart glasses with augmented reality during collaboration.

BEST MODE

The advantages and characteristics of the present invention, and a method for achieving the advantages and characteristics will become clear by referring to the exemplary embodiment, which is described in detail, together with the accompanying drawings. However, the present disclosure is not limited to exemplary embodiments disclosed herein but will be implemented in various forms, and the exemplary embodiments are provided so that the present disclosure is completely disclosed, and a person of ordinary skilled in the art can fully understand the scope of the present disclosure, and the present disclosure will be defined only by the scope of the appended claims. Throughout the specification, the same reference numeral indicates the same constituent element.

A term used in the present specification is for describing the exemplary embodiments, and does not intend to limit the present disclosure. In the present specification, a singular form includes a plural form as well, unless otherwise mentioned. Further, a term "comprises" and/or "comprising" used in the specification means that a corresponding characteristic and/or a constituent element exists, but it shall be understood that the existence or an addition of at least one of other characteristics, constituent elements, and/or a group thereof is not excluded.

A surgery assisting device using augmented reality according to an exemplary embodiment of the present invention will be described with reference to FIGS. 1 to 3. FIGS. 1 and 2 are diagrams illustrating partial configurations of a surgery assisting device using augmented reality according to an exemplary embodiment of the present invention. FIG. 3 is a conceptual diagram of the surgery assisting device using augmented reality according to the exemplary embodiment of the present invention.

Referring to FIGS. 1 to 3, the surgery assisting device using augmented reality according to the exemplary embodiment of the present invention includes a camera 10, wireless transmission equipment 30, smart glasses 70, and an AR server 100.

The camera 10 is a device for recording an affected area or a surgical site of a patient, and in some cases, with the help of a lighting 20, the camera 10 may more clearly record an image. In the meantime, the camera 10 may be a separate configuration from the smart glasses 70 which are s to be described below, or may also be in a form that is detachable from the smart glasses 70.

The wireless transmission equipment 30 is the equipment which receives the image recorded by the camera 10 in real time and transmits the received image to another device. In particular, the wireless transmission equipment 30 may provide the smart glasses 70 which are to be described below, with the image recorded by the camera 10, and thus, the affected area may be displayed on lenses 50 and 60 of the smart glasses 70.

Further, the wireless transmission equipment 30 may provide the AR server 100 with the image recorded by the camera 10, and the AR server 100 receiving the image may generate related augmented reality and then directly transmit the augmented reality or an image to which augmented reality is applied to the smart glasses 70 or transmit the augmented reality or an image to which augmented reality is applied to the wireless transmission equipment 30.

The smart glasses 70 are the glasses for displaying the image transmitted by the wireless transmission equipment 30 to the wearer. In more particular, the camera 10 may provide the recorded image to the wireless transmission equipment 30, and the wireless transmission equipment 30 receiving the image may display the image on the lenses 50 and 60 of the smart glasses 70.

Further, the image recorded by the camera 10 may be provided to the AR server 100 via the wireless transmission equipment 30, and the AR server 100 may generate augmented reality related to the received image and transmit the generated augmented reality or an image to which the augmented reality is applied to the wireless transmission equipment 30.

Then, the wireless transmission equipment 30 may display the image to which the augmented reality is applied on the lenses 50 and 60 of the smart glasses 70.

Otherwise, the AR server 100 may also display the image to which the augmented reality is applied on the lenses 50 and 60 of the smart glasses 70 without passing through the wireless transmission equipment 30.

The smart glasses 70 may include at least one of motion detecting sensors 40, such as a gyro sensor, a geomagnetic sensor, an angular velocity sensor, and a 6-axis sensor. Accordingly, the motion detecting sensor 40 may detect how a wearer of the smart glasses 70, such as a doctor, moves his/her head or face and the number of times of the attempt of each motion.

In particular, when the wearer turns his/her head or face to the left and right, moves his/her head or face back and forth, moves his/her head or face up and down, or rotates his/her head or face, the motion detecting sensor 40 may detect the motion.

Further, the motion detecting sensor 40 may detect whether each motion is performed only once or multiple times. According to another exemplary embodiment, when there are multiple motions, the motion detecting sensor 40 may detect a time interval between the motions.

The motions have different meanings, and various actions may occur by adjusting the shape of the wearer's face movement, the number of times of the attempt of each motion, the time interval between the motions, and the like.

For example, when a certain list tree is displayed on the lenses 50 and 60, an active display may move to the left or the right on the tree when the wearer turns his/her face left and right. Otherwise, when the wearer turns his/her face left and right, a new window located at the left side or the right side may also appear on the lenses 50 and 60.

Further, when the wearer moves his/her face up and down, an active display may move up and down on the tree.

Further, when the wearer moves his/her face forward once or several times, a certain item may be selected on the tree as a meaning of a click.

That is, the wearer wearing the smart glasses 70 may select a specific item or make a new window be displayed by moving his/her face left and right, back and forth, and up and down or moving his/her face left and right, and up and down within the tree on the lenses 50 and 60 depending on the number of times of the movement.

In the meantime, the specific face motion or the number of times of the motion may also mean storage of the image and transmission of the stored image.

The AR server 100 is the server for adding augmented reality to the image recorded by the camera 10 and providing the wearer with the augmented reality.

As described above, the image recorded by the camera 10 may be provided to the AR server 100 via the wireless transmission equipment 30, and the AR server 100 may generate augmented reality related to the received image and transmit the generated augmented reality or an image to which the augmented reality is applied to the wireless transmission equipment 30.

Then, the wireless transmission equipment 30 may display the image to which the augmented reality is applied on the lenses 50 and 60 of the smart glasses 70.

Otherwise, the AR server 100 may also display the image to which the augmented reality is applied on the lenses 50 and 60 of the smart glasses 70 without passing through the wireless transmission equipment 30.

Depending on the exemplary embodiment, the AR server 100 may analyze the image by utilizing an Artificial Intelligence (AI) function. In this case, the AR server 100 according to the exemplary embodiment may divide the image into segmentations according to a predetermined reference by using equipped AI. Further, the AR server 100 may categorize and classify the segmentations of the image divided by using AI for each corresponding predetermined reference. Depending on an exemplary embodiment, as the predetermined reference, various references, such as currently used surgical instrument, drugs used, surgical methods, surgical areas, whether an AR timer is used, history of participation in surgery, and profile, may be prepared, and when the AI of the AR server 100 determines that a portion of the entire recorded image corresponds to any one or more among the corresponding references, the AI of the AR server 100 may add mark information for the corresponding reference to the portion of the image and store the image. For example, in the case where "a surgical scene using surgical tool A" appears in the image, the AI of the AR server 100 may add mark information that "surgical tool A" to the image and store the image segmentation. Otherwise, when the use of anesthetic drug B is confirmed from an image at 10:03 and the use of anesthetic drug B is terminated at 10:08, the AI of the AR server 100 may separately divide the image from 10:03 to 10:08 as a segmentation, add mark information (for example, that may be a form of a hash tag— #anesthetic drug B, and the like) indicating anesthetic drug B to the divided image segmentation, and then divide and store the image segmentation as separate data.

In the meantime, the camera 10, the wireless transmission equipment 30, and the smart glasses 70 may be installed in an equipment holder 90, and display equipment 80 may be additionally installed in the equipment holder 90, so that the image recorded by the camera 10 or the image to which the augmented reality is added may be displayed.

Further, a leg part of the equipment holder 90 may adjusted in length, so that the equipment holder 90 may be height-adjusted as a whole.

A surgery assisting device using augmented reality according to another exemplary embodiment of the present invention may further include a data storage unit (not illustrated). The data storage unit may store the image recorded by the camera and/or the AR image generated by the AR server 100 by applying augmented reality to the image recorded by the camera.

In the foregoing, the surgery assisting device using augmented reality according to the exemplary embodiment of the present invention has been described, and hereinafter, the kind of augmented reality generated by the AR server 100 will be described in detail.

FIGS. 4 and 5 are diagrams illustrating an exemplary embodiment in which the surgery assisting device using augmented reality according to the exemplary embodiment of the present invention provides a surgery list tree.

Referring to FIGS. 4 and 5, the surgery assisting device using augmented reality according to the exemplary embodiment of the present invention may provide a surgery list tree.

When a surgery begins, the AR server 100 may provide a surgery list tree with augmented reality, and the surgery list tree may be displayed on the lenses 50 and 60 of the smart glasses 70.

The wearer may select a surgery item desired to be performed in the displayed surgery list tree, and when the wearer selects a specific surgery item, an image of the corresponding surgery method may be provided. In this case, the wearer may perform the surgery according to the provided image, so that the wearer may more easily and safely perform the surgery.

Reviewing the method of selecting, by the wearer, the surgery item desired to be performed in the displayed surgery list tree, the wearer may activate a surgery item to be applied to a patient in the surgery list tree by turning his/her face to the left and right, or adjusting the number of times of turning his/her face to the left or the right.

Then, when the wearer clicks the activated surgery item by moving his/her face forward or backward in the activated surgery item, a surgery method of the surgery item may be provided with augmented reality.

For example, referring to FIG. 5, when the wearer turns his/her face to the right twice, an activation indication may reach lung cancer and the lung cancer item may be activated. Then, the wearer may perform the click operation of moving his/her face forward once or twice to select the lung cancer item. As a result, a surgery method of the lung cancer may be provided to the lenses 50 and 60 as augmented reality.

FIG. 6 is a diagram illustrating an exemplary embodiment in which the surgery assisting device using augmented reality according to the exemplary embodiment of the present invention presents a surgery method based on a provided image.

Referring to FIG. 6, the surgery assisting device using augmented reality according to the exemplary embodiment of the present invention may present a surgery method based on the image provided by the camera 10.

During a surgery, the camera 10 may record an affected area or a surgical site and then provide the image to the wireless transmission equipment 30. The wireless transmission equipment 30 may transmit the received image to the AR server 100, and the AR server 100 may analyze the image by using the AI function and provide a required surgery method to the image with augmented reality.

Then, the wearer may select whether to use the surgery method provided by the AR server 100 by turning his/her face to the left and right, moving his/her face back and forth, or rotating his/her face, and when the wearer accepts the provided surgery method, the corresponding image may be provided with augmented reality.

Otherwise, the wearer may reject the surgery method provided by the AR server 100, and thus, the wearer may request another surgery method from the AR server 100 by turning his/her face to the left and right, moving his/her face back and forth, or rotating his/her face.

In the meantime, the AR server 100 may additionally propose a surgical tool according to the provided surgery method, and as a result, it is possible to prevent the wearer from accidently using the wrong surgical tool.

FIG. 7 is a diagram illustrating a case where the surgery assisting device using augmented reality according to the exemplary embodiment of the present invention emphasizes a surgical site.

Referring to FIG. 7, the surgery assisting device using augmented reality may emphasize a surgical site to the wearer. The surgery assisting device may provide an emphasis indication A, such as a square dotted line, with augmented reality on the area to be resected when an internal resection is performed, thereby enabling the wearer to accurately recognize the site to be resected. According to another exemplary embodiment, the surgery assisting device may display "time (for example, 3 seconds, 4 seconds, and the like) elapsed from the time of the resection to the present" on the incised site with augmented reality in real time.

As described above, the augmented reality may emphasize the site on which the surgery needs to be performed in the affected area, and when there are multiples sites on which the surgery needs to be performed, the augmented reality may sequentially emphasize the sites on which the surgery needs to be performed. In this case, the wearer may accurately recognize the order of the surgery, thereby preventing the wrong surgery.

FIG. 8 is a diagram illustrating a case where the surgery assisting device using augmented reality according to the exemplary embodiment of the present invention flashes information departing from a safety range among surgical information.

Referring to FIG. 8, the surgery assisting device using augmented reality may flash information departing from a safety range among surgical information.

The information provided with the augmented reality may be at least one of surgical information among a patient's pulse rate, blood pressure, an elapsed surgery time, and an anesthesia effective time, and the surgical information departing from the safety range among the surgical information may be flashed to warn the wearer.

For example, when the anesthesia effective time remains 50 minutes and the surgery needs to be terminated quickly, the surgery assisting device may flash the anesthesia effective time and warn the wearer that the available surgery time is short.

FIG. 9 is a diagram illustrating a case where the surgery assisting device using augmented reality according to the exemplary embodiment of the present invention presents an actual surgery progress state and an ideal surgery progress state to a wearer.

Referring to FIG. 9, the surgery assisting device using augmented reality may present an actual surgery progress state and an ideal surgery progress state to a wearer.

The AR server 100 may provide an ideal surgery progress state during the surgery to enable the wearer to compare an actual surgery progress state with the ideal surgery progress state.

In particular, when a specific part of the lung is resected during the surgery for lung cancer, augmented reality may be provided on the lenses 50 and 60 so that the wearer compares the actually resected site and a resection size D1 with an ideal resected site and a resection size D2. As the result of the comparison, when it is determined that the resected sites are the same or similar to each other and the resection sizes are the same or similar to each other, it can be confirmed that the surgery progress state is good.

FIG. 10 is a diagram illustrating an exemplary embodiment in which the surgery assisting device using augmented reality according to the exemplary embodiment of the present invention provides a collaboration list tree.

Referring to FIG. 10, the surgery assisting device using augmented reality may provide a collaboration list tree on the lenses 50 and 60 of the smart glasses 70.

The AR server 100 may provide a collaboration list tree with augmented reality, and the wearer may activate one or more desired collaboration items within the collaboration list tree by turning his/her face to the left and right, or adjusting the number of times of turning his/her face to the left or the right, and request the collaboration by clicking the activated collaboration item by moving his/her face forward or backward from in the activated collaboration items.

For example, referring to FIG. 10, when the wearer turns his/her face to the right twice, the activation indication may reach a neurosurgery item and the neurosurgery item may be activated. Then, the wearer may select the neurosurgery item by performing a click operation of moving his/her face forward once or twice. Then, the smart glasses 70 or the wireless transmission equipment 30 may transmit a collaborative medical treatment requesting signal to the selected neurosurgery.

Further, one or more collaboration items may be selected, and in addition to neurosurgery, the collaboration may be requested in the same manner from endocrine medicine.

FIG. 11 is a diagram illustrating the case where the surgery assisting device using augmented reality according to the exemplary embodiment of the present invention readjusts the order of a surgery method and provides the surgery method again.

Referring to FIG. 11, the surgery assisting device using augmented reality readjusts the order of a surgery method and provides the surgery method again.

The original order of the surgery method provided by the AR server 100 is step a, step b, step c, step d, and step e, but depending on the case, the wearer may not progress the surgery in the order of the surgery method provided by the AR server 100 by a predetermined selection of the wearer.

In this case, the AR server 100 may readjust the order of the surgery method in consideration of a surgery process progressed up to now, a state of a patient, and the like by utilizing AI and provide the surgery method again in the order of step a, step c, step d, step b, and step e.

In the meantime, depending on the case, when the wearer incorrectly progresses the order of the surgery method, the AR server 100 may recognize the incorrect progress and provide the order of the surgery method again in consideration of the incorrectly progressed state so as to solve the incorrect state and perform successful surgery.

FIG. 12 is a diagram illustrating a state where a surgery assisting device using augmented reality according to another exemplary embodiment of the present invention provides a plurality of smart glasses 70 with augmented reality during collaboration.

Referring to FIG. 12, the surgery assisting device using augmented reality may provide a plurality of smart glasses 70 with augmented reality.

When there are multiple wearers and thus there are multiple smart glasses 70, the AR server 100 may provide the plurality of smart glasses 70 with the same augmented reality or different augmented reality.

For example, collaboration is required during surgery, so that an operating surgeon and an anesthesiologist may each wear the smart glasses 70. In this case, the operating surgeon and the anesthesiologist may be located in the same operating room or in different spaces.

When collaboration is required, the contents of augmented reality required for the operating surgeon may be different from the contents of augmented reality required for the anesthesiologist, and thus, the AR server 100 may provide different augmented reality by providing the operating surgeon with augmented reality A and providing the anesthesiologist with augmented reality B.

In the meantime, depending on the case, different augmented reality may be provided to left and right lenses 50 and 60 of the smart glasses 70, and in this case, the wearer may receive various and more amount of augmented reality.

The surgery assisting device using augmented reality according to another exemplary embodiment of the present invention may be operated with a scenario below as a method of performing collaboration.

As described above, the data storage unit (not illustrated) may store (a) the recorded image recorded by the camera 10 and/or (b) the AR image generated by the AR server 100 by applying augmented reality to the recorded image. In this case, the AR server 100 according to the exemplary embodiment may categorize any one or both the recorded image and the AR image by using AI.

The "categorization of the image" according to the exemplary embodiment may be the operation of adding, by the AI of the AR server 100, category information to the corresponding image segmentation and classifying and storing the image segmentation based on a category in the case where (i) a plurality of category items for classifying the image is predetermined, and (ii) the segmentation of the recorded image and/or the AR image corresponds to at least one of the plurality of category items.

In this case, the category item according to the exemplary embodiment may include at least one of a type of surgical instrument, a type of drug used, a surgery method, a surgical area, whether an AR timer is used, and a profile of personnel participating in surgery. For example, a separate tag may be added to each surgical instrument, and the AI of the AR server 100 may check a surgical instrument used by recognizing the tag in the image, add category information (for example, a mark representing surgical instrument A) on the recognized surgical instrument to the image segmentation in which the recognized surgical instrument is used in the entire images, and then classify the corresponding image segmentation into the category corresponding to the recognized surgical instrument and store the corresponding image segmentation in the data storage unit.

In the meantime, when a collaborative medical treatment request is made during surgery or before/after surgery, the AR server 100 may select only an image required for a specialist subjected to the collaborative medical treatment request and provide the specialist with the selected image by using AI. In more particular, the AI of the AR server 100 may receive a collaborative medical treatment request signal from the wearer of the smart glasses 70. For example, the wearer may request collaboration from other medical staffs by adjusting the shape of the motion of the face and the number of times of the attempt of each motion. Otherwise, when it is determined that collaboration is required based on the predetermined surgery list tree, the surgery method, and the like, the AI of the AR server 100 may request the collaboration from other medical staffs. A reference for determining the need of the collaboration may be predetermined and stored in the AR server 100. Further, a selection reference for selecting the collaborative medical specialist subjected to the collaborative medical treatment request may be predetermined and stored in the AR server 100.

When the collaborative medical treatment request occurs, the AI of the AR server 100 may select an image segmentation determined to be necessary to the specialist (hereinafter, referred to as the "collaborative medical specialist") subjected to the collaborative medical treatment request among the image segmentations that are automatically classified and stored according to the predetermined reference and provide the specialist with the selected image segmentation. In this case, the AI of the AR server 100 may compare the information on the collaborative medical specialist with category information added to the image segmentations and provide the collaborative medical specialist with only the image segmentations having the matched information. For example, when it is necessary to request the collaboration from an anesthesiologist, the AI of the AR server 100 may read only the image segmentations to which category information (for example, "general anesthesia", "local anesthesia", and "incision") having relevancy to the anesthesiologist by a predetermined value or more is added among the classified image segmentations to which the category information is added, and transmit the read image segmentations to the anesthesiologist in real time or with a predetermined time difference from actual surgery. For example, the specialist who are requested to be collaborated may perform the collaboration after wearing the smart glasses, and the read image segmentations may be played on the smart glasses worn by the collaborative medical specialist. Otherwise, the collaborative medical specialist may perform the collaboration through a separate monitor, and the read image segmentations may be played on the monitor.

The exemplary embodiments of the present invention have been described with reference to the accompanying drawings, but those skilled in the art will understand that the present disclosure may be implemented in another specific form without changing the technical spirit or an essential feature thereof. Therefore, it should be understood that the aforementioned exemplary embodiments are all illustrative and are not limited.

The invention claimed is:

1. A surgery assisting device using augmented reality, comprising:
   a camera configured to record an affected area or a surgical site of a patient;
   wireless transmission equipment configured to receive and transmit an image recorded by the camera in real time;

smart glasses configured to display the recorded image transmitted by the wireless transmission equipment to a wearer;

an Augmented Reality (AR) server configured to add augmented reality to the recorded image and provide the smart glasses with an AR image to which the augmented reality is applied; and a data storage unit configured to store the recorded image recorded by the camera and the AR image, wherein the AR server categorizes any one or both of the image recorded by the camera and the AR image based on a predetermined category item, and the AR server classifies image segmentations, which are generated as a result of the performance of the categorization and to which category information is added, based on each category, and stores the classified image segmentations in the data storage unit, and wherein when a collaborative medical treatment request is generated, the AR server selects a collaborative medical specialist according to a predetermined collaborative medical specialist selection reference, compares information on the selected collaborative medical specialist with the category information added to the image segmentations, reads only image segmentations to which matched category information is added, and provides smart glasses worn by the selected collaborative medical specialist with the read image segmentations.

2. The surgery assisting device of claim 1, wherein the smart glasses includes at least one of motion detecting sensors among a gyro sensor, a geomagnetic sensor, an angular velocity sensor, and a 6-axis sensor, and the AR server provides a surgery list tree as augmented reality, activates a surgery item to be applied to a patient within the surgery list tree when a direction of movement of the wearer's face and a number of times of attempt of the direction of the movement are detected by the motion detecting sensors, and provides a surgery method of the surgery item with augmented reality when the activated surgery item is selected.

3. The surgery assisting device of claim 1, wherein the wireless transmission equipment provides the AR server with the image, and the AR server provides a required surgery method to the image with augmented reality.

4. The surgery assisting device of claim 3, wherein the smart glasses includes at least one of motion detecting sensors among a gyro sensor, a geomagnetic sensor, an angular velocity sensor, and a 6-axis sensor, and the smart glasses selects whether to use the surgery method provided by the AR server or requests another surgery method from the AR server based on a direction of movement of the wearer's face and a number of times of attempt of the direction of the movement.

5. The surgery assisting device of claim 2, wherein when the wearer does not progress the surgery in an order of the surgery method provided by the AR server, the AR server readjusts the order of the surgery method in consideration of information including a surgery process progressed up to now and a state of a patient by utilizing the AI function and provides the surgery method again.

6. The surgery assisting device of claim 2, wherein the AR server suggests a surgical tool according to the provided surgery method.

7. The surgery assisting device of claim 1, wherein the augmented reality is surgical information including at least one of a patient's pulse rate, blood pressure, an elapsed surgery time, and an anesthesia effective time, and surgical information departing from a safety range among the surgical information is flashed to warn the wearer.

8. The surgery assisting device of claim 1, wherein the augmented reality emphasizes a site on which the surgery needs to be performed in the affected area, and when there are multiple sites on which the surgery needs to be performed, the augmented reality sequentially emphasizes the sites on which the surgery needs to be performed.

9. The surgery assisting device of claim 1, wherein the smart glasses includes at least one of motion detecting sensors among a gyro sensor, a geomagnetic sensor, an angular velocity sensor, and a 6-axis sensor, the AR server provides a collaboration list tree with augmented reality, and the smart glasses activates a specific collaboration item within the collaboration list tree based on a direction of movement of the wearer's face and a number of times of attempt of the direction of the movement, and requests the collaboration from the AR server when the activated collaboration item is selected.

10. The surgery assisting device of claim 1, wherein when there are multiple wearers and there are multiple smart glasses, the AR server provides the plurality of smart glasses with the same augmented reality or different augmented reality.

11. The surgery assisting device of claim 1, wherein different augmented reality is provided to left and right lenses of the smart glasses.

12. The surgery assisting device of claim 1, wherein the category item includes at least one of a type of surgical instrument, a type of drug used, a surgery method, a surgical area, whether an AR timer is used, and a profile of personnel participating in surgery.

13. The surgery assisting device of claim 3, wherein when the wearer does not progress the surgery in an order of the surgery method provided by the AR server, the AR server readjusts the order of the surgery method in consideration of information including a surgery process progressed up to now and a state of a patient by utilizing the AI function and provides the surgery method again.

14. The surgery assisting device of claim 3, wherein the AR server suggests a surgical tool according to the provided surgery method.

15. The surgery assisting device of claim 2, wherein the augmented reality is surgical information including at least one of a patient's pulse rate, blood pressure, an elapsed surgery time, and an anesthesia effective time, and surgical information departing from a safety range among the surgical information is flashed to warn the wearer.

16. The surgery assisting device of claim 3, wherein the augmented reality is surgical information including at least one of a patient's pulse rate, blood pressure, an elapsed surgery time, and an anesthesia effective time, and surgical information departing from a safety range among the surgical information is flashed to warn the wearer.

* * * * *